United States Patent
Horiike et al.

(10) Patent No.: US 7,678,577 B2
(45) Date of Patent: Mar. 16, 2010

(54) BLOOD ANALYSIS APPARATUS AND BLOOD ANALYSIS METHOD

(75) Inventors: Yasuhiro Horiike, Ibaraki (JP); Akio Oki, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 458 days.

(21) Appl. No.: 11/659,599

(22) PCT Filed: Aug. 9, 2005

(86) PCT No.: PCT/JP2005/014882
§ 371 (c)(1),
(2), (4) Date: Jul. 23, 2007

(87) PCT Pub. No.: WO2006/016693
PCT Pub. Date: Feb. 16, 2006

(65) Prior Publication Data
US 2008/0028821 A1    Feb. 7, 2008

(30) Foreign Application Priority Data
Aug. 9, 2004    (JP)    ............... 2004-232638

(51) Int. Cl.
G01N 9/30    (2006.01)
B01D 21/00   (2006.01)
B01D 21/26   (2006.01)
B01L 3/02    (2006.01)
B01L 11/00   (2006.01)
B01L 3/00    (2006.01)
B01L 9/00    (2006.01)
G01N 21/00   (2006.01)

(52) U.S. Cl. .................. 436/45; 210/801; 210/787; 210/512.1; 422/100; 422/101; 422/102; 422/103; 422/72; 73/1.02

(58) Field of Classification Search .............. 436/45
See application file for complete search history.

(56) References Cited

U.S. PATENT DOCUMENTS

| 4,892,708 A | 1/1990 | Wogoman |
| 5,089,417 A * | 2/1992 | Wogoman .................. 436/45 |
| 5,798,272 A * | 8/1998 | Allen et al. ................ 436/169 |
| 2004/0158137 A1 * | 8/2004 | Eppstein et al. ........... 600/347 |

FOREIGN PATENT DOCUMENTS

JP    64-025058    1/1989

(Continued)

*Primary Examiner*—Jill Warden
*Assistant Examiner*—Timothy G Kingan
(74) *Attorney, Agent, or Firm*—Wenderoth, Lind & Ponack, L.L.P.

(57) ABSTRACT

A corpuscle/plasma separating part is disposed at the lower end of the substrate, and a sensor part connected to the corpuscle/plasma separating part is disposed at the upper end of the substrate, with a calibration solution reservoir being disposed on the lower side of the sensor part, and a calibration solution waste reservoir being disposed on the upper side of the sensor part. A first centrifugal axis is located upper to the corpuscle fraction storing part and lower to the plasma fraction storing part of the corpuscle/plasma separating part, while a second centrifugal axis is located within or close to the sensor part. Conveyance and discharge of the calibration solution can be carried out by performing centrifugation around the first centrifugal axis which is distant from the sensor part at a low speed of rotation, so that the centrifugal force exerted on the sensors would be small. During the centrifuge operation at a high speed of rotation for the separation of blood corpuscles, centrifugation can be performed around the second centrifugal axis so that the centrifugal force exerted on the sensors is small. Centrifuge operation allows separation of the blood corpuscles and blood plasma, and conveyance of the blood plasma and the calibration solution, as well as certain discharge of the calibration solution from the sensors, thereby allowing precise analysis. Any damage in the sensors due to strong centrifugal force during the separation of blood corpuscles and blood plasma can be prevented.

21 Claims, 12 Drawing Sheets

FOREIGN PATENT DOCUMENTS

| | | |
|---|---|---|
| JP | 2001-258868 | 9/2001 |
| JP | 2003-083926 | 3/2003 |
| JP | 2003-083958 | 3/2003 |
| JP | 2004-109099 | 4/2004 |
| WO | 00/53317 | 9/2000 |
| WO | WO 2004/027391 * | 1/2004 |
| WO | 2004/074846 | 9/2004 |

* cited by examiner

BLOOD ANALYSIS APPARATUS AND BLOOD ANALYSIS METHOD

TECHNICAL FIELD

The present invention relates to a blood analysis apparatus consisting of microgroove flow channels produced on a substrate made of insulating materials such as a quartz plate, a polymer resin plate or the like. In particular, the invention relates to the structure of the substrate and flow channels for performing conveyance of liquids such as a calibration liquid for an analytic sensor, blood, or the like, by means of centrifugal force, when a trace amount (a few µl or less) of blood is introduced to the groove flow channels on the substrate, is subjected to centrifuge, and is separated into the corpuscle component and the plasma component, and then the concentrations of various chemicals in the plasma component are measured.

BACKGROUND ART

Physical examination or diagnosis of disease states has been conventionally carried out by collecting a large amount, such as several cubic centimeters, of blood from a patient, and using the measurement values obtained from large scale automated blood analysis apparatuses in the analysis of the collected blood. In general, such automated analysis apparatuses are available in medical institutions such as hospitals, and are large in size, and their operation is limited to those who are technically qualified.

However, in recent years, there is a growing tendency for the development and practicalization of a new device which can instantly inform the health status of an examinee, by arranging various analytic apparatuses such as sensors on a substrate having a size of a few millimeters to a few centimeters at maximum at each side of rectangle, as a result of application of the microprocessing technique used in the production of highly advanced semiconductor devices, and introducing a body fluid of the examinee, such as blood. Development of such low-priced devices allows an attempt to reduce the ever-increasing health insurance benefits by enabling daily health management of aged people at home in the on-coming aging society, and so on. Further, such devices are expected to have various social effects, such as that in the field of emergency medicine, if the presence or absence of any infectious disease (hepatitis, acquired immune deficiency, etc.) in an examinee, etc. could be quickly judged by using the device, appropriate action would be possibly taken in response; thus, much attention is being paid to this technical field. As such, instead of the conventional automated analytic apparatuses, small scaled and convenient blood analysis method and blood analysis apparatus, which are aimed at performing blood analysis personally at home, are under development (See, for example, Patent Document 1).

Patent Document 1: JP-A No. 2001-258868

FIG. 1 shows an example of the micromodularized blood analysis apparatus described in Patent Document 1. Symbol 101 represents a lower substrate of the blood analysis apparatus, on which at microgroove flow channel (microcapillary) 102 formed by etching is formed. Over this lower substrate 101, an upper substrate (not shown in the figure) of almost the same size is glued together to seal the groove flow channel 102 from the outside.

Along the flow channel 102, there are sequentially formed a blood collecting means 103, a plasma separating means 104, an analyzing means 105 and a transporting means 106, from the uppermost stream part to the lowermost stream part.

The blood collecting means 103 at the forefront part of the flow channel is equipped with a hollow blood collecting needle 103a, and this blood collecting needle 103a is pricked into the body and is used as an inlet for blood into the substrate. The separating means 104 is a bend formed in the middle of the flow channel 102 and consists of, for example, a U-shaped microcapillary. The collected blood is led to this U-shaped microcapillary, and then the substrate is subjected to acceleration in a certain direction by a centrifuge, thereby the blood corpuscle component being precipitated at the lowest part of the U-shape, and the blood plasma being separated as supernatant. The analyzing means 105 are sensors for measuring the pH value and the respective concentrations of oxygen, carbon dioxide, sodium, potassium, calcium, glucose, lactic acid and the like in the blood.

The transporting means 106 which is disposed at the lowermost stream of the flow channel is intended to transport the blood in the microcapillary by electroosmotic flow, and consists of electrodes 107 and 108, and a portion of flow channel 109 connecting the two electrodes. The electroosmotic flow which is generated when voltage is applied between the electrodes, transports the buffer solution that has been preliminarily filled in the flow channel, to the downstream side of the flow channel, and the suction force generated thereby allows uptake of the blood from the collecting means 103 at the forefront part of the flow channel 102 into the substrate. This suction force also drives the blood plasma obtained by centrifuge into the analyzing means 105.

Symbol 110 represents an output means for taking out information from the analyzing means, and consists of electrodes and the like. Symbol 111 represents a control means for controlling the collecting means, plasma separating means, analyzing means, transporting means and output means, as necessary.

The blood collected from the collecting means 103 is separated into the plasma component and the corpuscle component at the separating means 104, and this blood plasma is led to the analyzing means 105, where the pH value and the respective concentrations of oxygen, carbon dioxide, sodium, potassium, calcium, glucose, ureic nitrogen, creatinine, lactic acid and the like in the blood plasma are measured. The transportation of blood between the respective means is carried out by the transporting means 106 having an ability for pumping, such as by means of electrophoresis or electroosmotic phenomenon or the like. In FIG. 1, the downstream region of the flow channel 102 is branched into 5 subregions, and each of these subregions has the analyzing means 105 and the transporting means 106 formed therein.

In many cases, glass materials such as quartz have been used for the substrate of such blood analysis apparatus. However, in consideration of their suitability for mass production of the apparatus at low costs, and the ease of disposal after use, resin materials have been recently put to use.

The conventional blood analysis apparatus illustrated in FIG. 1 requires a transporting means such as an electroosmotic pump 106 for introducing a blood sample into the apparatus. In every substrate, after obtaining blood plasma by centrifuging the introduced blood, it is required to re-operate the electroosmotic pump 106 in order to transport the blood plasma to the analyzing means 105. Furthermore, when the analyzing means are, in particular, sensors established on the basis of the principles of electrochemistry, these sensors need to be calibrated in advance using a calibration solution. That is, before leading the blood plasma into the sensors, these sensors should be immersed in the calibration solution to carry out calibration of the sensors, and the calibration solution should be discharged from the analyzing means after calibration. Such transportation of the calibration solution also requires the transporting means such as a pump.

For the transporting means, it can be considered to use electroosmotic pumps formed on the same substrate as shown in FIG. 1, or negative pressure pumps installed outside the substrate. These transporting means allow transportation of the blood, or the blood plasma, calibration solution and the like, by pneumatic transportation or suction. Here, in order to transport a desired liquid to a desired site in the blood analysis apparatus, it is necessary to precisely control the suction force of the transporting means and the like. In this regard, sensors for liquid position should be newly installed in the blood analysis apparatus or outside the apparatus, but addition of such controlling instruments or position sensors has been causing a problem of making the apparatus expensive.

When the analyzing means are sensors established on the basis of the principles of electrochemistry, the sensors should be calibrated with a calibration solution (reference solution) containing the components to be tested at known concentrations, and then this calibration solution should be discharged from the analyzing means. However, even after discharging the calibration solution, there may be residual calibration solution remaining on the surface of the analyzing means or flow channel means, depending on the wettability of the surface. As described above, since the blood analysis apparatus being presently discussed is intended to analyze the concentrations of various chemicals present in a trace amount, such as about a few microliters, of blood, the size of the means constituting the apparatus, such as the flow channel means, is diminished. In general, when the size of an object is decreased, the ratio S/V of the surface area (S) and volume (V) increases, and this implies that the effect of the surface is significantly exhibited. Therefore, there has been a problem that even though the amount of the calibration solution remaining on the surface of the flow channel means or analyzing means is a trace amount, that amount of the residual calibration solution has an impact on the fluctuation of the concentrations of measured chemicals in an analysis apparatus in which the amount of the blood plasma introduced is minimal. To this end, it is required that only after the calibration solution is certainly discharged out of the analyzing means, the blood plasma is introduced to the analyzing means.

In consideration of the above-described circumstances, the present inventors have suggested a blood analysis apparatus for performing plasma separation in the flow channel by centrifuge operation, which enables conveying of the blood, blood plasma and calibration solution in the apparatus without using pumps or the like, and which enables precise analysis by certainly discharging the calibration solution from the sensor part (see, for example, Patent Document 2).

Patent Document 2: Japanese Patent Application No. 2003-040481

FIG. 2 illustrates an example of the blood analysis apparatus described in Patent Document 2 (unpublished). Symbol 201 represents an upper substrate in which a flow channel is formed, and symbol 202 represents a lower substrate in which sensor electrodes 203 or electrode terminals 204 for taking the sensor signals out of the system are formed. The upper substrate 201 is equipped with a blood collecting needle 205, and the collected blood is transported from an opening for suction and pneumatic transportation 208 to a blood reservoir 207 through a guiding flow channel 206 by means of an external pump (not shown in the figure). A flow channel 209 and flow channel 210 are connected to opening holes 211 and 212, respectively, which are formed on a side wall of the upper substrate 201. However, upon the suction of blood, the opening holes 211 and 212 are closed by a holder (not shown in the figure) on which the blood analysis substrate is mounted. Likewise, a calibration solution reservoir 213 stores a calibration solution introduced from the opening for suction and pneumatic transportation 208.

Exemplary operation of this already-suggested blood analysis apparatus substrate will be described in the following. First, when the blood analysis apparatus substrate is centrifuged around the central axis of the first centrifugal force 214, the calibration solution in the calibration reservoir 213 is taken into a plurality of sensor grooves 217 housing a plurality of sensors 203, through guiding flow channels 215 and 216. After calibration of the sensors 203, the blood analysis apparatus substrate is rotated 90 degrees clockwise and mounted on the centrifuge. That is, when the substrate is centrifuged around the central axis of the second centrifugal force 218 which is located on the left side of FIG. 2, the calibration solution filling the sensor grooves 217 flows through guiding flow channels 216 and 219 and is stored in a calibration solution waste reservoir 220.

Then, the blood analysis apparatus substrate is rotated 90 degrees counterclockwise and mounted on the centrifuge. That is, when the substrate is centrifuged around the central axis of the first centrifugal force, 214, the blood from the blood reservoir 207 is conveyed to the sensor grooves 217 through a guiding flow channel 221. When the centrifugal force is continuously applied as such, the corpuscle component in the blood is fractionated in the direction to which gravity is applied, that is, down to the lower side of the sensor grooves 217, and the plasma component is separated to the upper side of the sensor grooves 217 as a supernatant. A group of sensors 203 are disposed in this region, so that the pH value and the respective concentrations of oxygen, carbon dioxide, sodium, potassium, calcium, glucose, lactic acid and the like in the blood are measured by an external measuring instrument through a plurality of electrode terminals 204 connected to the respective sensors.

This already-suggested blood analysis apparatus can be subjected to centrifuge operation in two different directions, and allows conveyance of the calibration solution in the calibration solution reservoir to the sensor part by centrifuge operation in the first centrifugal direction, and after the calibration of sensors, certain discharge of the calibration solution from the sensor part by centrifuge operation in the second centrifugal direction. After the discharge of the calibration solution, centrifuging in the first centrifugal direction allows conveyance of the blood in the blood reservoir to the sensor part, as well as separation of the blood into the corpuscles and the plasma.

However, even with these advantageous, the blood analysis apparatus was found to have unignorable problems in carrying out blood analysis in short time due to the use of centrifugal force.

It is definitely critical that the measurement time to be taken by a blood analysis apparatus chip should be as short as possible. In the present blood analysis apparatus, the distance from the central axis of centrifugal force to the center of the chip is 5 cm, and the time normally required for infusion or discharge of the calibration solution is about 1 second, even with a small centrifugal force of 3000 rpm or less. However, in order to separate the corpuscles and the plasma in the blood in a few seconds to a few minutes, a centrifugal force of at least 4000 rpm or greater is required at the region of corpuscle separation. FIG. 12 shows the relationship between the speed of rotation (rpm) and the acceleration (G) at this time, in which 3000 rpm corresponds to application of gravitational acceleration of 500 G, and 4000 rpm corresponds to application of gravitational acceleration of 1000 G.

It was found that the output of the sensors is reduced by the centrifuge operation upon the separation of blood corpuscles and blood plasma. For example, when a calibration solution (containing 137 mM sodium ions) was measured with a sodium ion sensor, the output voltage was affected by the speed of rotation (rpm) during centrifuge, as shown in FIG. 3. The sensor output indicated a stable value of about 200 mV up to a speed of rotation of about 3000 rpm; however; at a higher speed of rotation, the sensor output showed a tendency to decrease, and at the same time, the distribution of the value increased. In the present measurement, sensors exhibiting a stable value of about 200 mV up to 1000 rpm were provided and used for the respective rotation tests. Although not particularly mentioned, the same tendency was observed in the measurement of potassium ions.

In a sodium ion concentration measuring sensor, bis(12-crown-4) of the ion sensing membrane capturing sodium ions, and an anion scavenging agent which takes the role of preventing anions in the blood plasma from penetrating into the sensing membrane are mixed with PVC (polyvinyl chloride), and this mixture is immobilized on a carbon electrode to be used as the sensor. Here, in order to make it easier to introduce sodium ions into the sensing membrane, a large amount of plasticizer is mixed into the PVC. When the centrifugal force at 7000 rpm is estimated from the weight of one sensor, the force exerted on the sensor is in the order of pico-newtons. However, it is conjectured that the cause of such reduction in the sensor output at the high speed of rotation might involve deformation of the PVC membrane, which includes the ion sensing membrane and contains the plasticizer, on the carbon electrode due to the strong centrifugal force, thereby a part of the PVC membrane delaminating from the carbon electrode and allowing water penetration. It can be considered to harden the membrane by altering the membrane composition and to strengthen the immobilization of membrane onto the carbon electrode; but, hardening of the membrane may lead to loss of the original characteristics of the electrochemical sensor.

DISCLOSURE OF THE INVENTION

The present invention has been achieved in consideration of such circumstances, and it is a first aspect of the invention to provide a blood analysis apparatus for performing blood plasma separation by centrifuge operation, which allows conveyance of the blood plasma and the calibration solution in the apparatus without using pumps or the like, allows certain discharge of the calibration solution from the sensor part, and enables analysis with high precision since the sensors are not damaged by the centrifuge operation upon separation of the blood plasma.

It is a second aspect of the invention to provide a blood analysis method, which allows conveyance of the blood plasma and the calibration solution in the apparatus only by centrifuge operation, allows certain discharge of the calibration solution from the sensor part, and also enables analysis with high precision since the sensors are not damaged by the centrifuge operation upon separation of the blood plasma, when the blood analysis apparatus for performing blood plasma separation by centrifuge operation is used.

According to the invention, the first aspect is achieved by a blood analysis apparatus for performing plasma separation of a whole blood sample by centrifugation and for analyzing the components to be tested in the liquid blood component, which includes:

(a) a corpuscle/plasma separating part disposed at the lower end of the substrate, including a corpuscle fraction storing part to precipitate the blood corpuscle fraction under the action of centrifugal force and to store the corpuscle fraction, and a plasma fraction storing part located on the upper side of the corpuscle fraction storing part to store the blood plasma, (b) a sensor part disposed at the upper end of the substrate, having sensor grooves housing the sensors to analyze the components to be tested, (c) a plasma guiding flow channel connecting the corpuscle/plasma separating part and the sensor part, (d) an inlet for blood to introduce a whole blood sample to the corpuscle/plasma separating part, (e) a calibration solution reservoir to store a calibration solution for the calibration of sensors, (f) a calibration solution waste reservoir to store the calibration solution after the calibration of sensors, (g) a calibration solution introducing flow channel to connect the calibration solution reservoir and the sensor grooves, and (h) a calibration solution discharging flow channel to connect the sensor grooves and the calibration solution waste reservoir;

wherein centrifugation can be performed around a first centrifugal axis which is located upper to the corpuscle fraction storing part and lower to the upper end of plasma fraction storing part; while centrifugation can be performed around a second centrifugal axis which is located within or close to the sensor part than corpuscle/plasma separating part; and wherein the calibration solution reservoir is located on the lower side of the sensor part and on the upper side of the first centrifugal axis, and the calibration solution waste reservoir is located on the upper side of the sensor part.

Thus, the blood analysis apparatus of the invention can be centrifuged around two different centrifugal axes, and conveyance and disposal of the calibration solution are carried out by centrifuging around the first centrifugal axis which is distant from the sensor part, at a low speed of rotation with a large radius of centrifugation, so that the gravitational acceleration exerted to the sensors would be small. On the other hand, in the centrifuge operation to exert greater gravitational acceleration for the separation of blood corpuscles, the centrifugal axis of this operation (the second centrifugal axis) is located within or close to the sensor part in order to reduce the gravitational acceleration exerted onto the sensor part, so that the centrifugation to exert large gravitational acceleration on the corpuscle/plasma separating part does not result in exertion of large gravitational acceleration on the sensor part. Thereby, any damage in the sensors due to excessive centrifugal force exerted thereon can be prevented.

Here, in a preferred embodiment, the corpuscle/plasma separating part is formed as a U-shaped flow channel, in which the corpuscle fraction storing part is formed at the bend of the lowest end, while the plasma fraction storing part is formed upper thereto. The corpuscle fraction storing part may be formed to protrude downward from the lowest end of the U-shaped flow channel, and in this case, the volume is preferably made larger than the amount of the corpuscle fraction in the whole blood sample introduced into the U-shaped flow channel. The inlet for blood can be formed on a side wall of the U-shaped flow channel, upper to the plasma fraction storing part.

It is also desirable to form an air venting flow channel in the U-shaped flow channel so that the whole blood sample may be introduced more easily to the lowest end of the U-shaped flow channel, and the most preferred embodiment has this air venting flow channel connected to the lowest end of the U-shaped flow channel.

A plurality of sensor grooves may be formed in the sensor part, and each sensor groove may have a plurality of sensors for analyzing various components to be tested. In this case, when the sensor grooves are arranged in a circumferential shape, with the center of the circle being taken as the second centrifugal axis, that is, when the sensor grooves are arranged radially around the second centrifugal axis, at the time of carrying out the corpuscle/plasma separation by centrifuge operation around the second centrifugal axis, the distance between the sensor and the center of the centrifuge is shortest, and the gravitational acceleration exerted on the sensor can be minimized.

The inlet for plasma may be made capable of mounting a blood collecting instrument which stores collected blood, on the inlet. When the inlet for plasma or the corpuscle/plasma separating part is kept hydrophilized, introduction of blood sample or conveyance of blood plasma can be carried out smoothly. Likewise, when the plasma guiding flow channel, sensor grooves, as well as the calibration solution reservoir, calibration solution waste reservoir, calibration solution introducing flow channel and calibration solution discharging flow channel are respectively kept hydrophilized, conveyance of the calibration solution and conveyance of blood plasma may become smoother.

The second aspect of the invention is achieved by a blood analysis method comprising the following steps:

(1) providing a blood analysis apparatus, which includes a corpuscle/plasma separating part disposed at the lower end of the substrate, including a corpuscle fraction storing part to precipitate the blood corpuscle fraction under the action of centrifugal force and to store the corpuscle fraction, and a plasma fraction storing part located upper to the corpuscle fraction storing part to store the blood plasma; a sensor part disposed at the upper end of the substrate, having sensor grooves housing the sensors to analyze the components to be tested; a plasma guiding flow channel connecting the corpuscle/plasma separating part and the sensor part; an inlet for blood to introduce a whole blood sample to the corpuscle/plasma separating part; a calibration solution reservoir to store a calibration solution for calibration of the sensors; a calibration solution waste reservoir to store the calibration solution after the calibration of sensors; a calibration solution introducing flow channel to connect the calibration solution reservoir and the sensor grooves; and a calibration solution discharging flow channel to connect the sensor grooves and the calibration solution waste reservoir;

(2) introducing the calibration solution in the calibration solution reservoir into the sensor grooves by centrifuging the blood analysis apparatus around a first centrifugal axis which is located upper to the corpuscle fraction storing part and lower to the upper end of the plasma fraction storing part;

(3) performing calibration of the sensors;

(4) discharging the calibration solution in the sensor grooves to the calibration solution reservoir by centrifuging the blood analysis apparatus around the first centrifugal axis;

(5) performing separation of the blood corpuscles and blood plasma in the corpuscle/plasma separating part, and precipitating the blood corpuscle fraction in the corpuscle fraction storing part, by introducing a whole blood sample into the corpuscle/plasma separating part and centrifuging the blood analysis apparatus around a second centrifugal axis, which is located closer to the sensor part than the corpuscle/plasma separating part;

(6) conveying the blood plasma fractionated in the plasma fraction storing part to the sensor grooves by centrifuging the blood analysis apparatus around the first centrifugal axis; and (7) performing analysis of the liquid component of the blood plasma in the sensor grooves by means of the sensors.

During the process of introducing the calibration solution at step (2), the process of discharging the calibration solution at step (4) and the process of conveying the blood plasma at step (6), where centrifugation is carried out around the first centrifugal axis, it is desirable that the gravitational acceleration exerted on the sensors is 500 G or less. Also, during the process of separating the blood corpuscles and blood plasma at step (5), where centrifugation is carried out around the first centrifugal axis, it is desirable that the gravitational acceleration exerted on the corpuscle/plasma separating part is 1000 G or greater, while the gravitational acceleration exerted on the sensors is 500 G or less.

When an air venting flow channel is formed at the plasma fraction storing part of the blood analysis apparatus, during the process of conveying the blood plasma at step (6), the blood plasma may be conveyed to the sensor part by introducing an external gas under pressure from this air venting flow channel, without performing centrifuge operation.

REFERENCE NUMERALS

Figure 1:
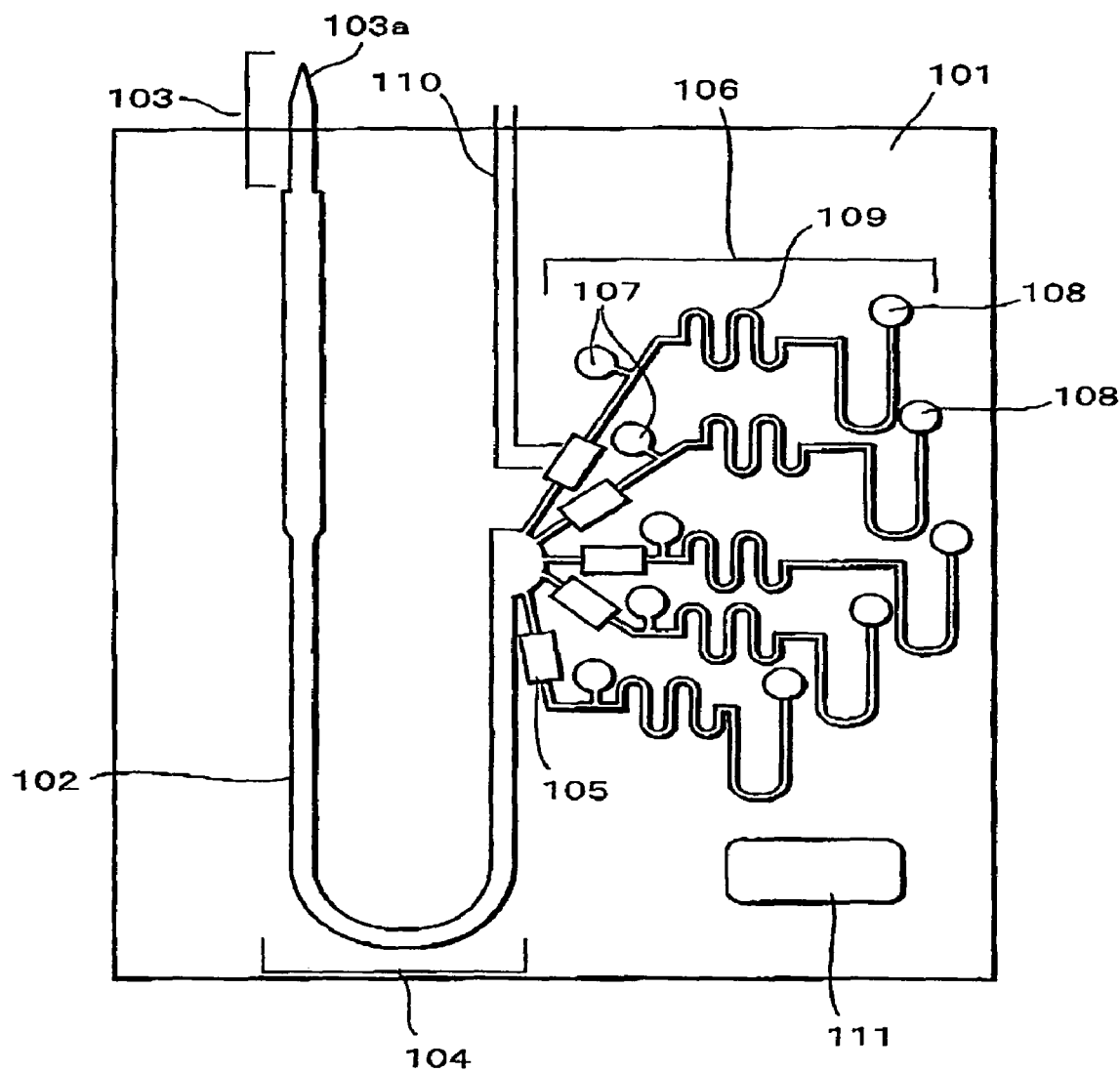
FIG. 1 is a conceptual diagram illustrating an example of a conventional micromodularized blood analysis apparatus.
Figure 2:
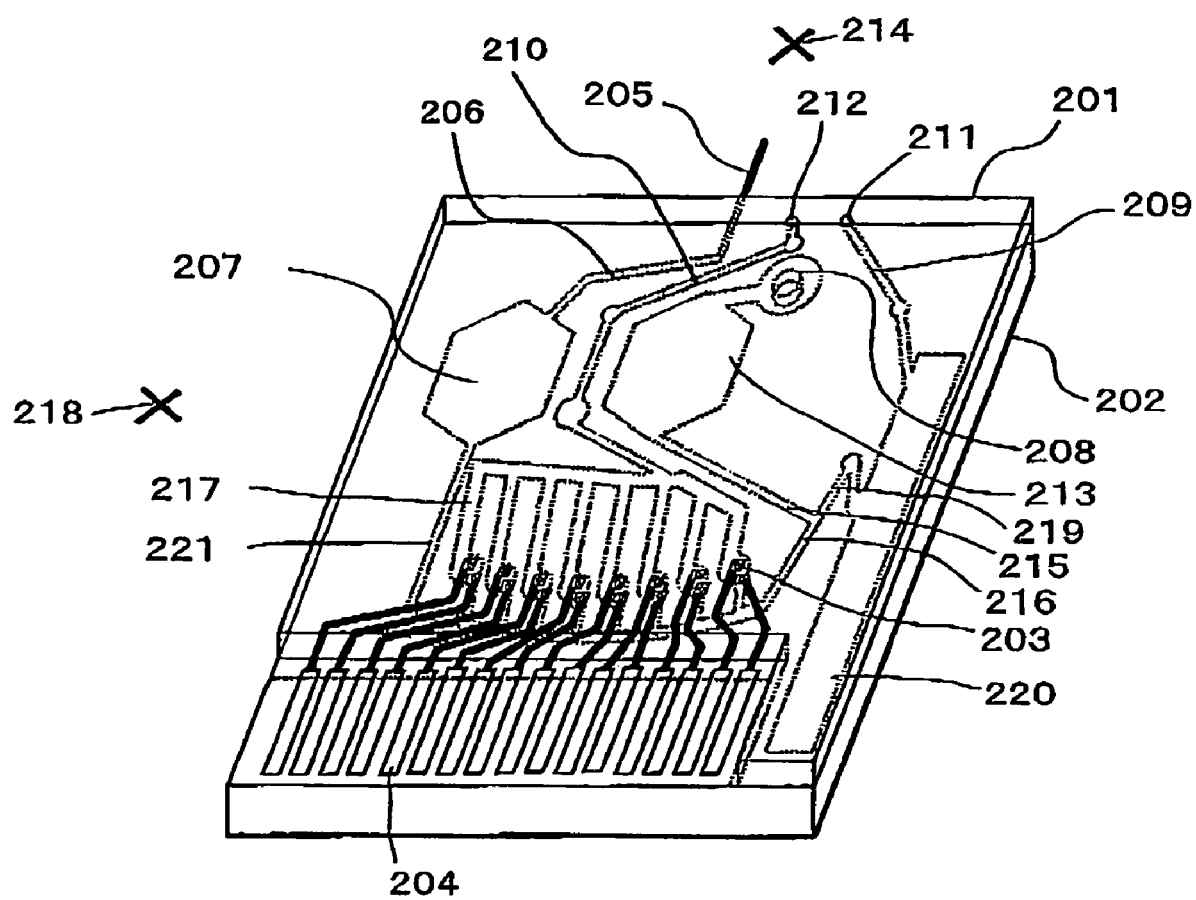
FIG. 2 is an overall perspective view of a blood analysis apparatus suggested by the inventors (not published).
Figure 3:
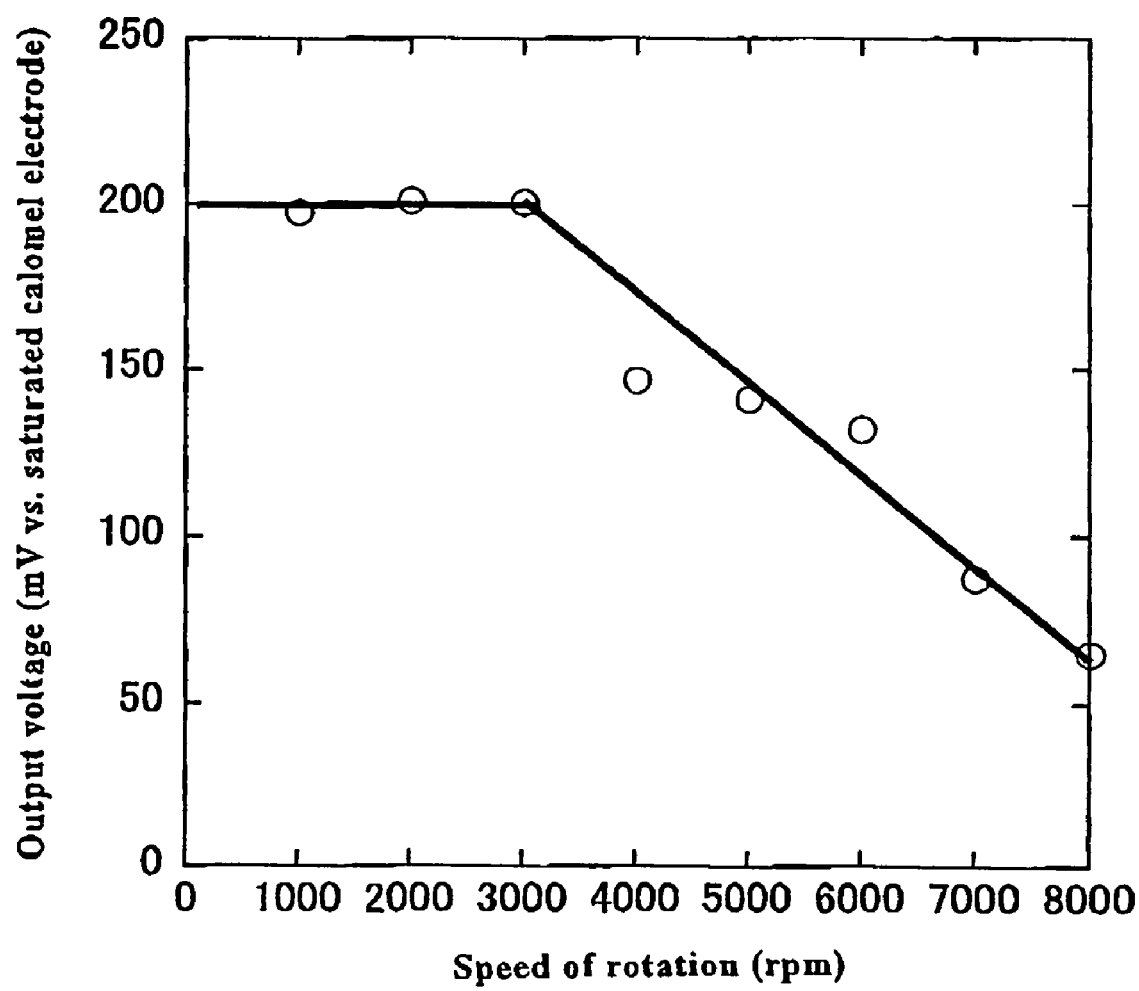
FIG. 3 is a diagram indicating the change of the output voltage with the speed of centrifugal rotation (rpm) when the calibration solution (containing 137 mM sodium ions) is measured with a sodium ion sensor.

10: blood analysis apparatus (substrate)
12: U-shaped flow channel (corpuscle/plasma separating part)
14: blood corpuscle reservoir (corpuscle fraction storing part)
16: plasma fraction storing part
18: inlet for blood
20: blood collecting instrument
28: air venting flow channel
29: air venting hole
30, 30A, 30B: sensor part
32, 32A, 32B: sensor groove
34: sensor
38: external electrode terminal
40: blood plasma guiding flow channel
42: calibration solution reservoir
44: calibration solution introducing flow channel
46: calibration solution waste reservoir
48: capillary valve (calibration solution discharging flow channel)
50, 52: flow channel for air relief
60: rotating vessel
62: substrate guiding groove
C0: central axis of rotation of rotating vessel
C1: first centrifugal axis (center of centrifugal force)
C2: second centrifugal axis (center of centrifugal force)

BEST MODE FOR CARRYING OUT THE INVENTION

Figure 4:
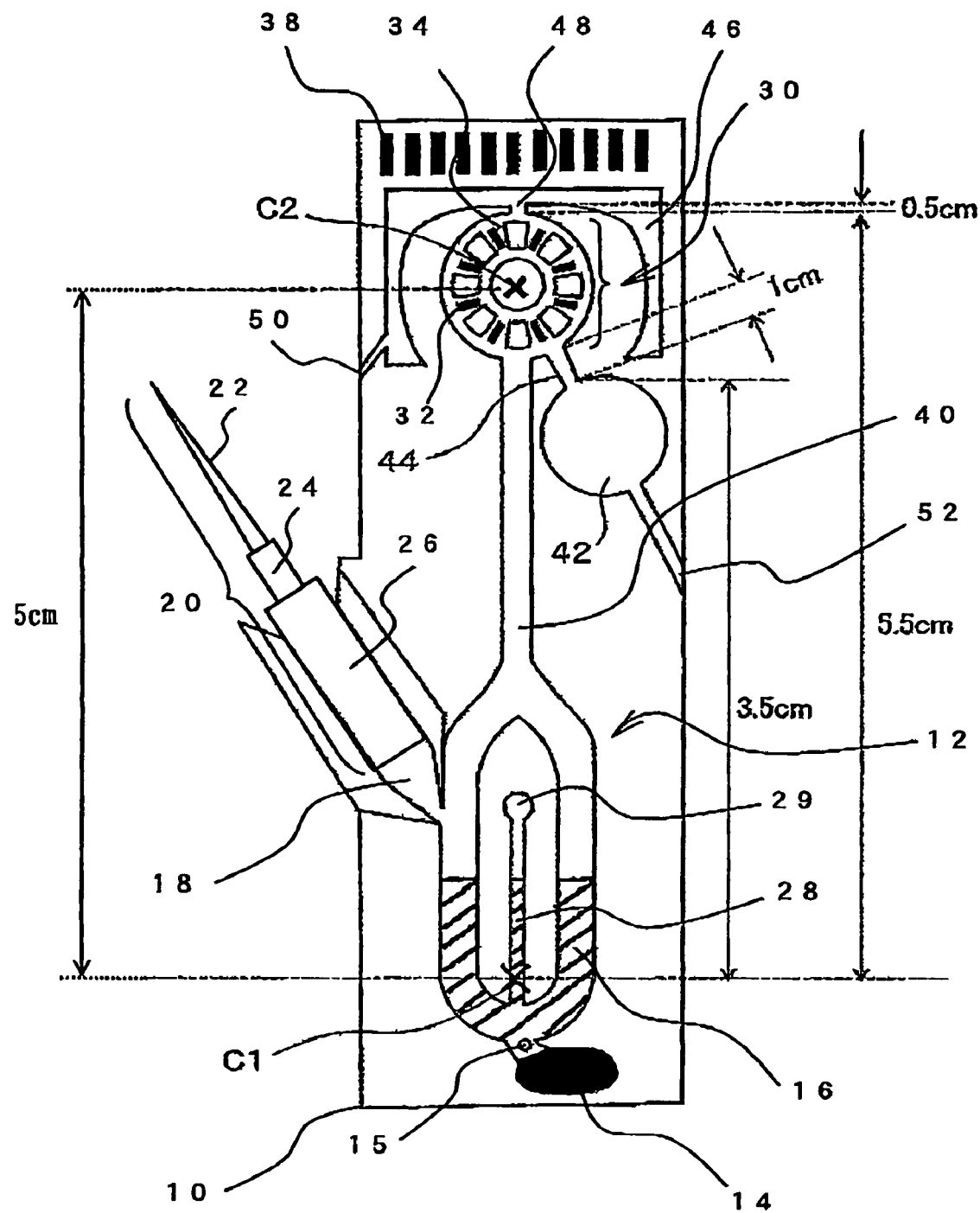
FIG. 4 is a schematic planar view of the blood analysis apparatus according to an embodiment of the present invention.

FIG. 4 is a schematic planar view of the blood analysis apparatus according to an embodiment of the present invention. Symbol 10 represents the substrate of a blood analysis apparatus formed longitudinally in the diagram, in which a substrate having a flow channel formed thereon is superposed on a substrate having sensor electrodes or wiring formed thereon, and the diagram indicates the internal flow channel structure. The upper and lower substrates are made of, for example, resins such as polyethylene terephthalate (PET) or polycarbonate (PC). Within the substrate 10, a corpuscle/plasma separating part 12 having a U-shaped flow channel at the lower end is disposed, and a corpuscle reservoir 14 as a corpuscle fraction storing part is formed at the bend of the lowest end. The upper part of the corpuscle reservoir 14 is used as a plasma fraction storing part 16 in which the blood plasma is fractionated as supernatant during centrifugation. Symbol 15 represents a backflow stop to prevent the blood corpuscles precipitated in the corpuscle reservoir (corpuscle fraction storing part) 14 from flowing backward during handling of the substrate. FIG. 4 illustrates the status after the corpuscle/plasma separating operation, while the dark filled portion in the corpuscle reservoir 14 represents the fractionated blood corpuscles. The shaded portion of the plasma fraction storing part represents the fractionated plasma.

An inlet for blood 18 for introducing a whole blood sample is formed on a side wall of the U-shaped flow channel 12, upper to the plasma fraction storing part 16, and this inlet is capable of mounting thereon a blood collecting instrument 20 which stores collected blood. The blood collecting instrument 20 comprises a stainless steel painless needle 22, a stainless steel tube 24 for reinforcing the needle, and a primary blood reservoir 26 for storing blood after blood collection, all integrated into one body, and is inserted into the inlet for blood 18 of the substrate 10 which has undergone complete sensor calibration operation. Symbol 28 represents an air venting flow channel which is connected to the lowest end of the U-shaped flow channel, and makes the introduction of the whole blood sample from the inlet for blood 18 smooth.

A first centrifugal axis C1 is located upper to the corpuscle fraction storing part 14 and lower to the upper end of the plasma fraction storing part 16. The plasma fraction located upper to this centrifugal axis C1 is conveyed to the below-described sensor part 30 by centrifuge operation. Therefore, the position of this first centrifugal axis C1 is determined in accordance with the amount of the conveyed plasma fraction.

The sensor part 30 is disposed on the upper end side of the substrate 10, and has a plurality of sensor grooves 32 which are disposed radially around a second centrifugal axis C2 as the center. Each of the sensor grooves 32 houses a sensor 34, and the output of the sensor is induced through the respective wiring to an electrode terminal 38, which is exposed to the outside of the substrate. The sensor 34 consists of, for example, an electrode made of silver/silver chloride, carbon or the like, and a reference electrode made of silver/silver chloride. The wiring is made of, for example, silver-containing carbon, while the external electrode 38 is made of, for example, silver. Such the silver/silver chloride or carbon electrode, the silver/silver chloride reference electrode, the silver-containing carbon wiring, the silver electrode, and the like are formed by, for example, screen printing.

Symbol 40 represents a plasma guiding flow channel integrating the upper part of the U-shaped flow channel 12 and connecting to the sensor part 30, and conveys the blood plasma fractionated in the plasma fraction storing part 16 after the corpuscle/plasma separating operation, to the sensor part 30. Symbol 42 represents a calibration solution reservoir storing a calibration solution for calibrating the sensors, and is connected to the sensor part 30 through a calibration solution introducing flow channel 44. The calibration solution reservoir 42 is located lower to the sensor part 30 and upper to the first centrifugal axis C1. Thus, when the substrate 10 is centrifuged around the first centrifugal axis C1, the calibration solution in the calibration solution reservoir 42 is conveyed to the sensor part 30.

A calibration solution waste reservoir 46 is formed on the upper side of the sensor part 30, and is connected to the sensor part 30 through a calibration solution discharging flow channel 48 (the below-described capillary valve), In FIG. 4, the calibration solution waste reservoir 46 is disposed so as to surround the sensor part 30, but it is sufficient if the capacity of the part upper to the sensor part 30 is at least larger than the amount of the calibration solution discharged thereto. Symbols 50 and 52 represent air venting flow channels.

Figure 5:
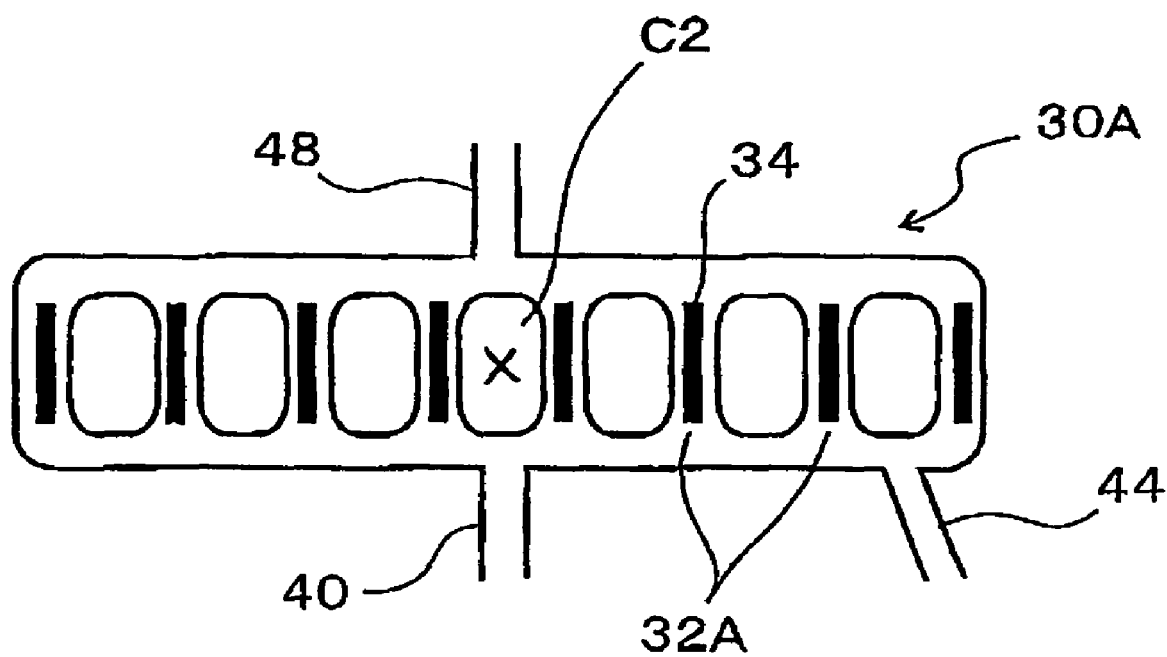
FIG. 5 is a schematic diagram illustrating another exemplary disposition of sensor grooves.
Figure 6:
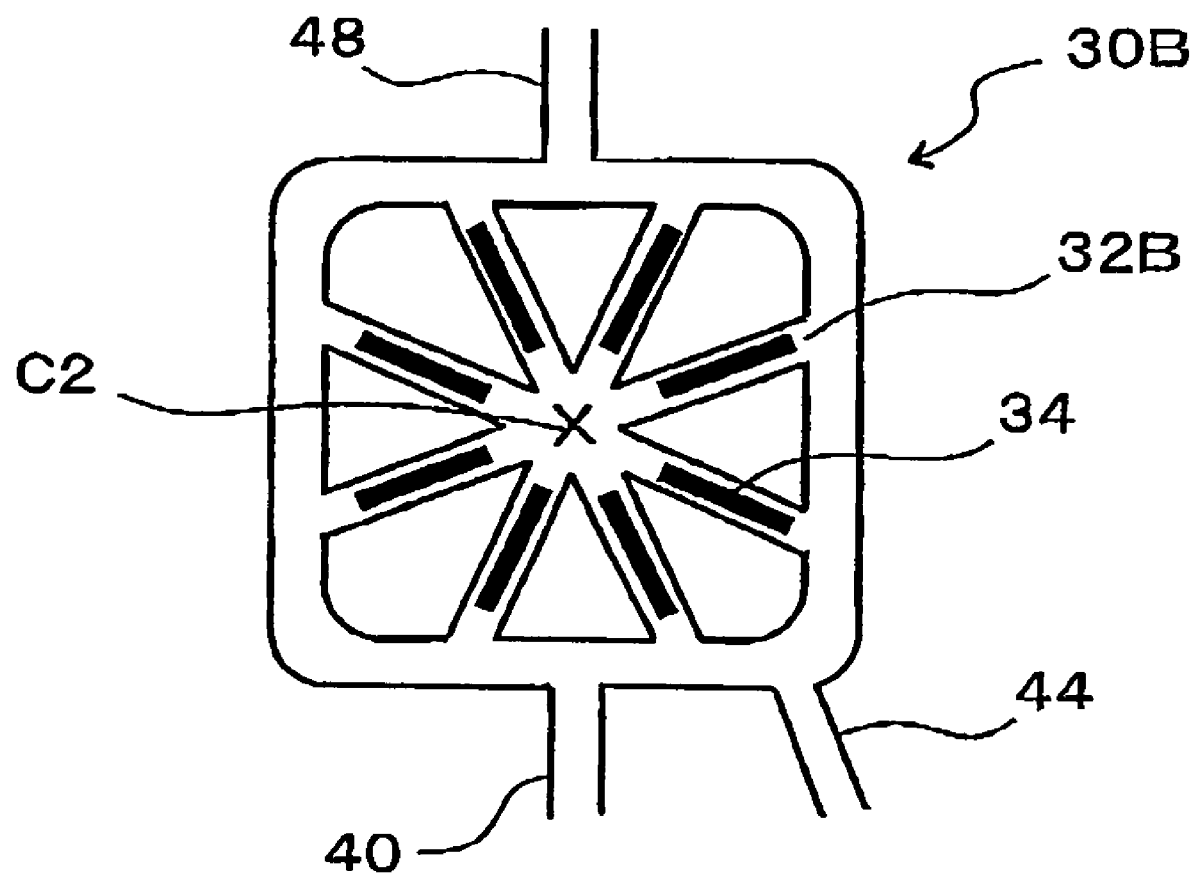
FIG. 6 is a schematic diagram illustrating another exemplary disposition of sensor grooves.

In the present embodiment, the sensor grooves 32 in the sensor part 30 are radially arranged, but as shown in FIG. 5, sensor grooves 32A may be arrayed laterally, with the second centrifugal axis C2 positioned at the center, to form the sensor part 30A. Furthermore, as shown in FIG. 6, the external wall of the sensor part 30B may be made rectangular, and sensor grooves 32B may be arranged radially therein. In FIGS. 4, 5 and 6, the second centrifugal axis C2 is disposed within the sensor parts 30, 30A and 30B, because such disposition makes it convenient to reduce the gravitational acceleration exerted onto the sensors as much as possible. The second centrifugal axis C2 can reduce the gravitational acceleration exerted on the sensors as long as the position of the axis is close to the sensor part 30, even if not necessarily disposed within the sensor part 30.

Figure 7:
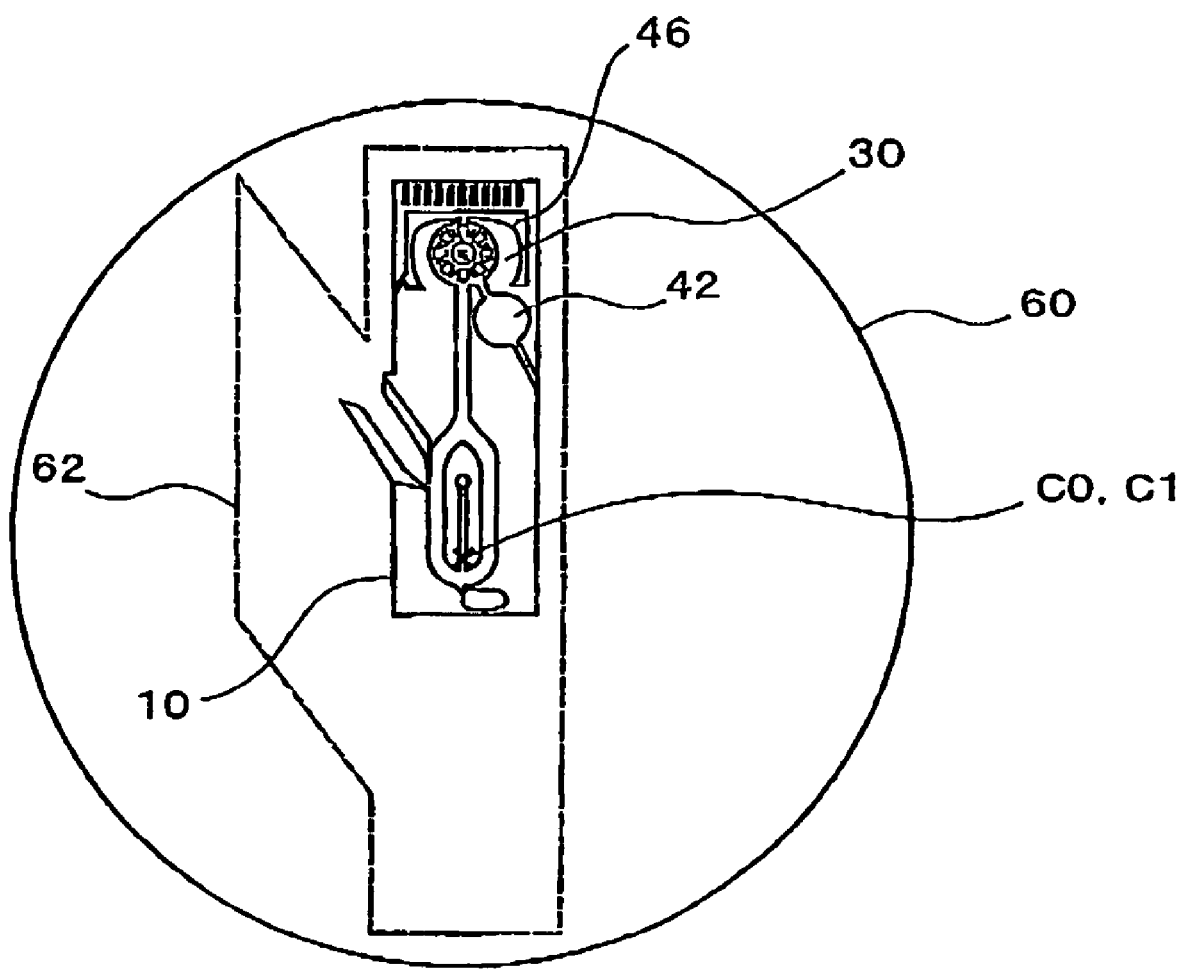
FIG. 7 is a diagram illustrating the status of the blood analysis apparatus mounted on a rotating vessel during the process of introducing the calibration solution and the process of discharging the calibration solution, in an embodiment of the blood analysis method according to the invention.
Figure 8:
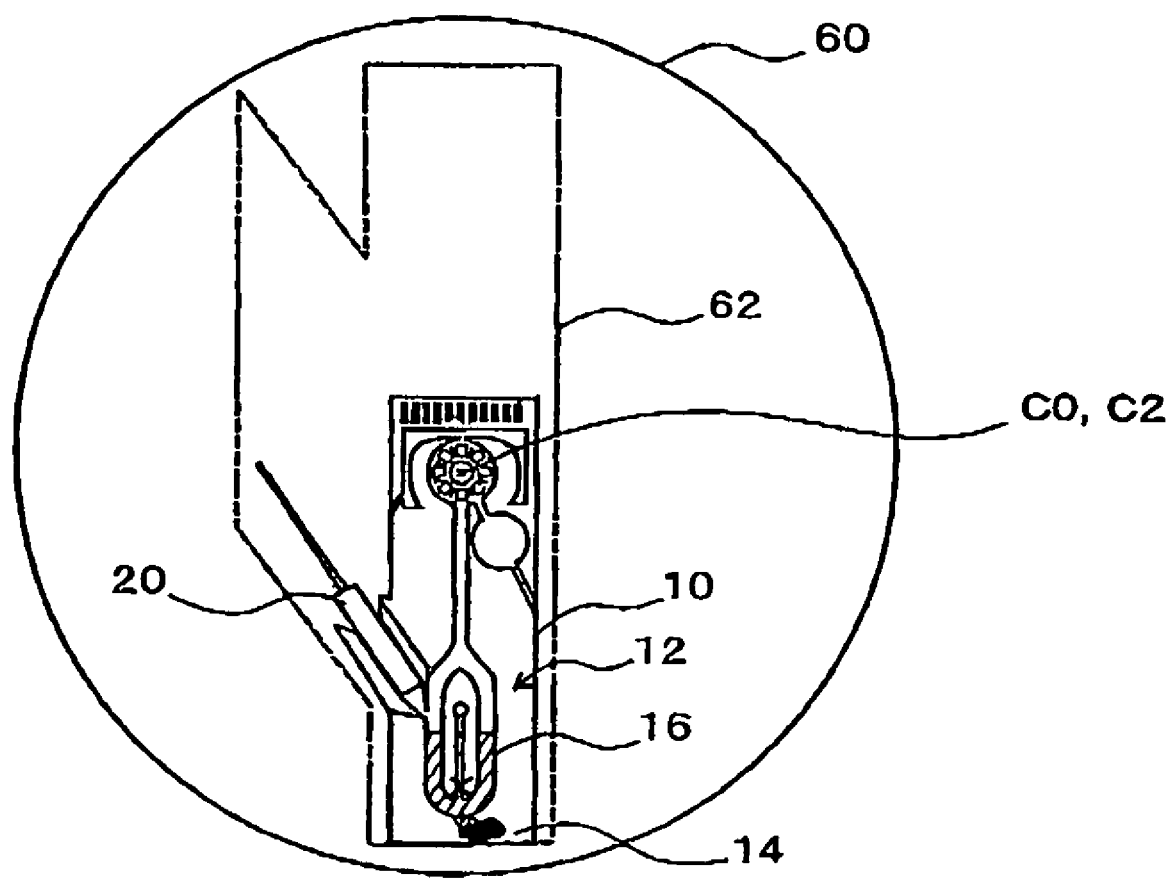
FIG. 8 is similarly a diagram illustrating the status of the blood analysis apparatus mounted on a rotating vessel during the process of separating the blood corpuscles and blood plasma.

The method of using this blood analysis apparatus will be described with reference to FIGS. 7 through 9. First, calibration of sensors is carried out prior to the analysis of blood. As shown in FIG. 7, the substrate 10 of the blood analysis apparatus is placed in a guiding groove 62 formed on the rotating vessel 60 in the direction along the diameter, mounted upward, and is fixed such that the position of the rotatory axis C0 of the rotating vessel 60 corresponds to the first centrifugal axis C1 of the substrate 10. When the substrate 10 is centrifuged in this state, the calibration solution in the calibration solution reservoir 42 is conveyed to the sensor part 30. Here, air in the sensor part 30 is discharged from the air venting flow channel 52. The speed of centrifugal rotation at this time is set at a speed of rotation such as that the calibration solution does not pass through the capillary valve 48. After stopping centrifugation, calibration of each sensor is carried out on the rotating vessel 60.

After performing calibration of the sensors, the calibration solution in the sensor grooves 32 is discharged. After the sensor calibration, the position of the substrate 10 is maintained, and the rotating vessel 60 is rotated again to centrifuge the substrate 10, and the calibration solution in the sensor part 30 is discharged to the calibration solution waste reservoir 46. This centrifuge operation enables removal of the calibration solution covering over the sensors, thus eliminating any error occurring in the measured values due to residual calibration solution. Furthermore, in this process of discharging the calibration solution, centrifugation is performed at a higher speed of rotation than that for the centrifugation during the process of conveying the calibration solution previously carried out, so that the calibration solution passes through the capillary valve 48. However, it is desirable that the centrifugation is performed with a gravitational acceleration such as that the sensors are not damaged by the centrifugal force, and it is also desirable that the centrifugal force exerted on the sensor part 30 is 500 G or less.

Next, introduction of a whole blood sample and separation of the blood corpuscles and blood plasma are carried out by centrifuge operation. The blood collecting instrument 20 is inserted into the inlet for blood 18 of the substrate 10, and the substrate 10 in this state is moved downward inside the guiding groove 62 and is fixed such that the second centrifugal axis C2 corresponds to the position of the rotatory axis C0 of the rotating vessel 60 (FIG. 8). When the substrate 10 is centrifuged in this state, the whole blood sample is conveyed into the U-shaped flow channel 12, and is subjected to separation of the blood plasma and blood corpuscles. The corpuscle fraction is fractionated into the corpuscle reservoir 14, while the plasma fraction is fractionated into the upper part of the U-shaped flow channel 12 (plasma fraction storing part 16) as supernatant. The centrifuge operation at this time is carried out in order to completely separate the blood corpuscles, and it is desirable that a centrifugal force of 1000 G or greater is exerted on the lowest part of the U-shaped flow channel.

Figure 9:
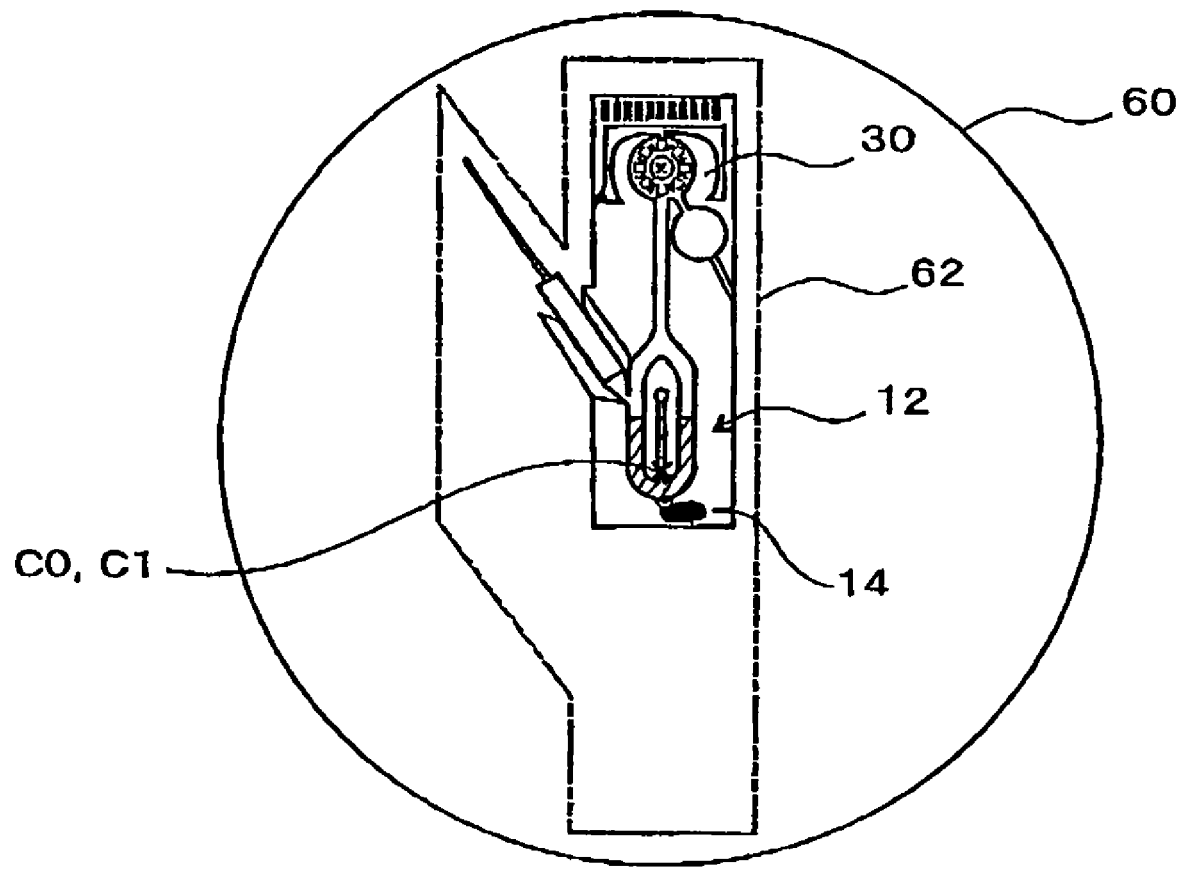
FIG. 9 is similarly a diagram illustrating the status of the blood analysis apparatus mounted on a rotating vessel during the process of conveying the blood plasma.

After the separation of blood corpuscles, the substrate 10 is moved upward again inside the guiding groove 62 and is fixed such that the first centrifugal axis C1 corresponds to the position of the rotatory axis C0 of the rotating vessel 60 (FIG. 9). When the substrate 10 is centrifuged in this state, the blood plasma that is located upper to the centrifugal axes C0 and C1 shown in FIG. 9 is conveyed to the sensor part 30 by centrifugal force. The corpuscle reservoir 14 is located lower to the centrifugal axes C0 and C1, and the blood corpuscles fractionated therein are never transferred to the sensor part 30. The centrifuge operation at this time is preferably carried out with a gravitational acceleration such as that the sensors are not damaged, and it is also desirable that the centrifugal force exerted on the sensor part 30 is 500 G or less. Finally, each component to be tested in the blood plasma is measured by each of the sensors.

An important aspect of the present embodiment is that the centrifugal axis used in the process of introducing the calibration solution and the centrifugal axis used in the process of discharging the calibration solution are all the first centrifugal axis C1 (FIG. 7). When the calibration solution is introduced from the calibration solution reservoir 42 to the sensor part 30, the calibration solution conveyed to the sensor part 30 should not be transferred further to the calibration solution waste reservoir. That is, it is necessary to estimate the relatively weak centrifugal used in the process of introducing the calibration solution, the flow channel diameter of the calibration solution introducing flow channel 44 and the flow channel diameter of the capillary valve (calibration solution discharging flow channel) 48, and also to estimate the relatively strong centrifugal force conveying the calibration solution to the calibration solution waste reservoir 46 through the capillary valve 48 after the calibration.

Figure 10:
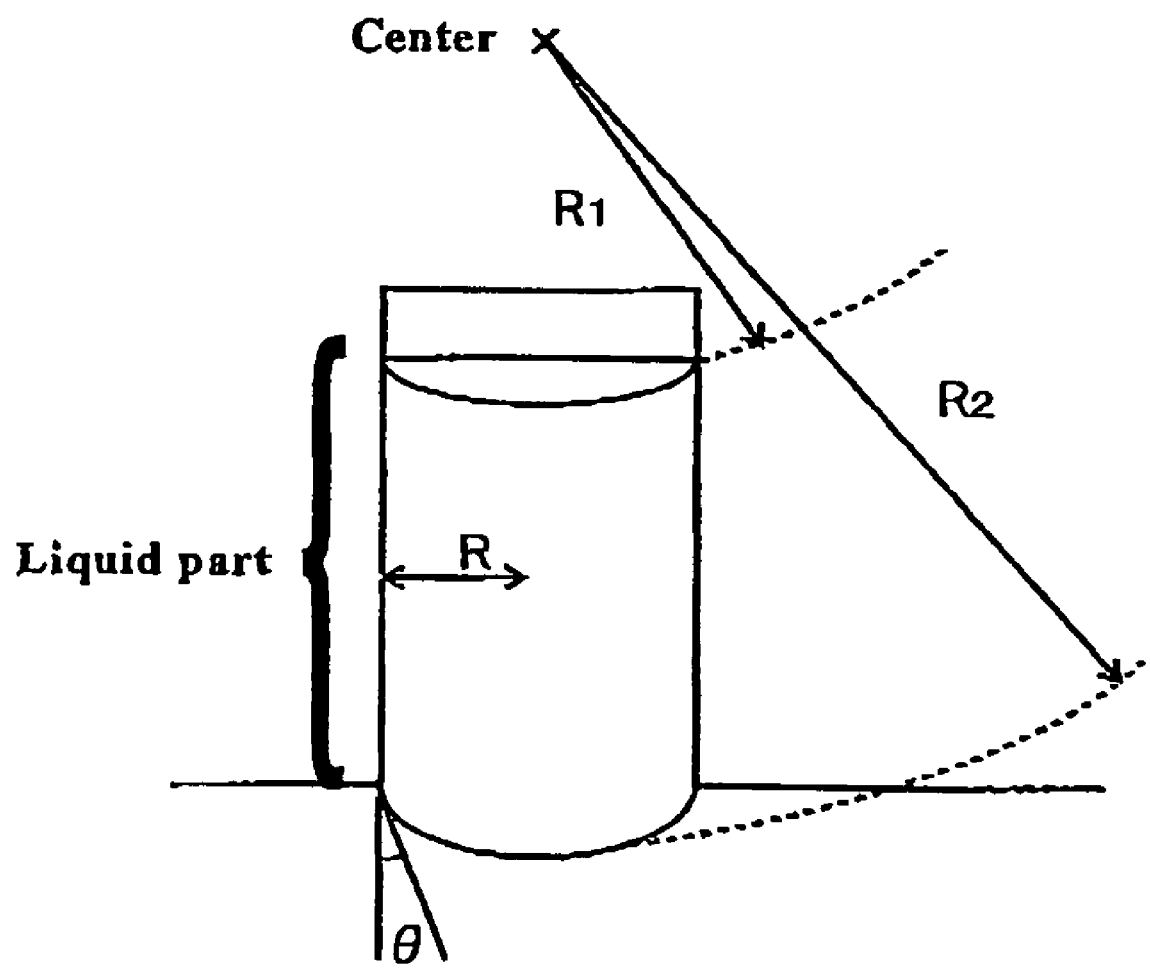
FIG. 10 is a diagram illustrating the parameters needed for determining the speed of rotation when a solution is discharged from a capillary by centrifugal force.

Description with regard to the capillary valve is found in page 315 of [Fundamentals and Applications of Microfluidics] written by Nam-Trung Nguyen and Steven T. Wereley (publisher: Artech House (Boston-London) 2002). As shown in FIG. 10, when a solution is present in between radius $R_1$ and radius $R_2$ from the centrifugal center in the capillary tube; and when the contact angle of the solution to the capillary tube when the solution is discharged from the capillary tube is $\theta$, the surface tension is $\gamma$, the radius of the capillary tube is R, and the density of the solution is $\rho$, the following relationship is found between these parameters and the minimum speed of rotation fm required by the solution to project from the capillary tube by centrifugal force:

$$fm^2 \geq \gamma \cos\theta / R \cdot \rho \cdot \pi^2 \cdot (R_2 - R_1)(R_2 + R_1)$$

Figure 11:
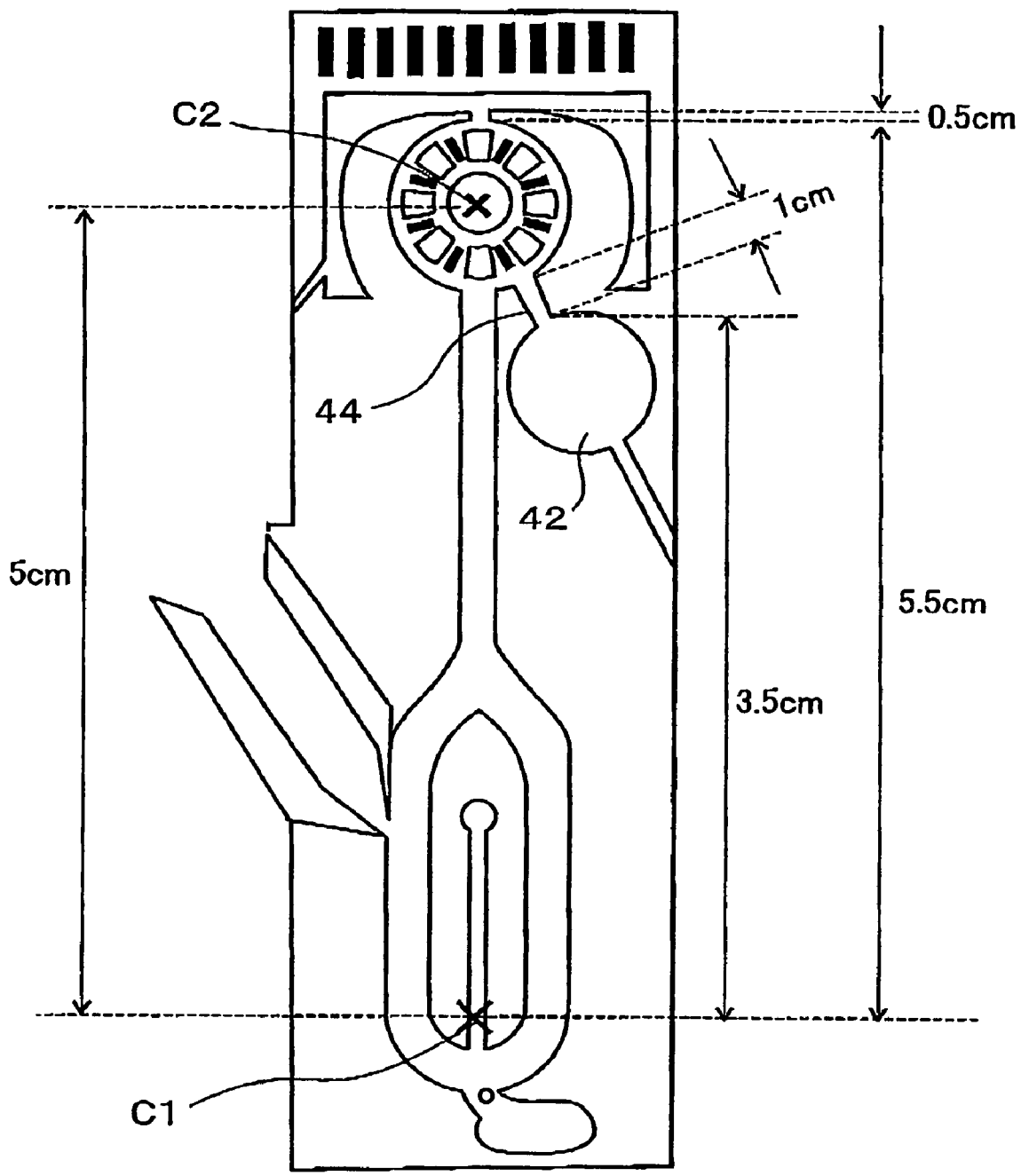
FIG. 11 is a diagram illustrating all of the parameters needed for calculating the speed of rotation to introduce the calibration solution by centrifugal force, and the speed of rotation to discharge the calibration solution through a capillary valve, in an embodiment of the blood analysis apparatus according to the invention.

As shown in FIG. 11, the distance between the first centrifugal axis C1 and the second centrifugal axis C2 is set to 5 cm; the flow channel length $(R_2-R_1)$ of the flow channel from the calibration solution reservoir 42 through the flow channel to the groove housing the sensor (i.e., calibration solution introducing flow channel 44) is set to 1 cm; and the distance from the first centrifugal axis C1 to the end of the calibration solution reservoir 42 on the side of the sensor part 30 ($R_1$) is 3.5 cm. The surface tension ($\gamma$) of water at 25° C. is $72\times10^{-3}$ [N/m], and when polyethylene terephthalate resin is used as the material for the substrate 10, the contact angle $\theta$ with water is 80 degrees. The density ($\rho$) of water is $1\times10^3$ [kg/m$^3$]. When these values are used, even if the minimum speed of rotation (fm) is set to 100 rpm, the diameter (2R) of the calibration solution discharging flow channel 44 is sufficient only with about 3 μm or greater. That is, when the diameter of the calibration solution introducing flow channel is set to 3 μm or greater, with the flow channel length being 1 cm, conveyance of the calibration solution from the calibration solution reservoir 42 to the sensor part 30 is made possible by centrifugation at 100 rpm around the first centrifugal axis C1.

Figure 12:
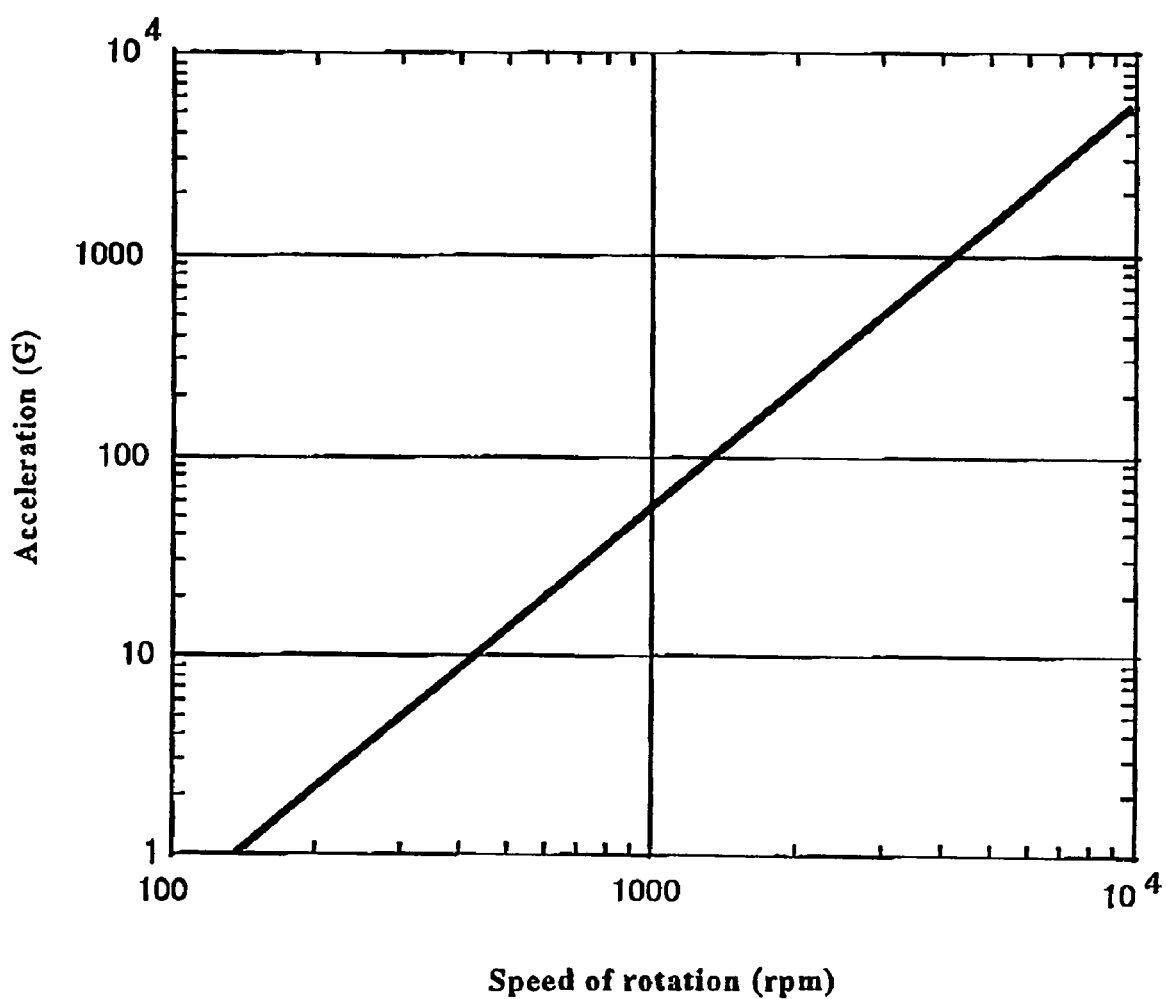
FIG. 12 is a diagram indicating the relationship between the gravitational acceleration (G) generated upon rotation of a rotating body having a radius of 50 mm, and the speed of rotation (rpm).

On the other hand, when the flow channel length $(R_2-R_1)$ of the capillary valve 48 is set to 0.5 cm, and the diameter (2R) is set to about 100 μm, the calibration solution at the sensor part (sensor groove) flows into the calibration solution waste reservoir 46 when fm is about 1000 rpm or greater. Here, since the gravitational acceleration exerted on the sensor is about 60 G from FIG. 12, since the centrifugal radius to the sensor is about 5.5 cm. In fact, a blood analysis apparatus substrate produced in such flow channel dimension exhibited normal operation in the flows of the calibration solution and the blood plasma.

An advantage of this blood analysis substrate is that the sensors are disposed at a radial position about 5 mm away from the second centrifugal axis C2. This distance is one-tenth of the distance of about 5 cm from the first centrifugal axis C1. In the case of centrifuging around the second centrifugal axis C2, only about one-tenth of the centrifugal force is exerted on the sensors, as compared with the case of centrifuging around the first centrifugal axis C1. Therefore, although centrifugation was carried out at 7000 rpm around the second centrifugal axis in the centrifuge operation during the process of separating the blood corpuscles as shown in FIG. 8, the sensors were not affected by any damage.

Moreover, in the process of conveying the blood plasma, as shown in FIG. 9, the corpuscle reservoir 14 is located on the opposite side of the plasma guiding flow channel 40, with the centrifugal axis C0 (first centrifugal axis C1) being interposed in between, and only the blood plasma could be conveyed to the sensor part, without the blood corpuscles flowing backward to the plasma guiding flow channel 40. In the present embodiment, although the substrate 10 was moved from the position of FIG. 7 to the position of FIG. 9 due to the conveyance of the blood plasma after the separation of blood corpuscles, the blood plasma can be conveyed to the plasma guiding flow channel 40 and the sensor part 30, when air is introduced from the air venting hole 29 of the air venting flow channel 28 after the separation of blood corpuscles (See FIG. 4).

INDUSTRIAL APPLICABILITY

As such, the blood analysis apparatus of the present invention can be centrifuged around two different centrifugal axes, and it is possible to carry out introduction and discharge of a calibration solution into sensor grooves, separation of blood corpuscles, and introduction of blood plasma into the sensor part only by centrifugal force, without ever using pumps. There is no need to use conventional negative pressure pumps, and a simple blood analysis apparatus of low price can be realized. Conveyance and disposal of the calibration solution are carried out by centrifuging around the first centrifugal axis which is distant from the sensor part, at a low speed of rotation, so that the gravitational acceleration exerted to the sensors would be small. On the other hand, in the centrifuge operation to exert large gravitational acceleration for the separation of blood corpuscles, centrifugation around the second centrifugal axis may lead to reduction of the gravitational acceleration exerted on the sensor part. Therefore, there is no possibility for the sensors, which are multilayered and comprise heterogeneous components, to be damaged by strong centrifugal force upon the separation of blood corpuscles, and more precise analysis can be performed.

The invention claimed is:

1. A blood analysis apparatus for separating the blood plasma from a whole blood sample by centrifugation and analyzing the components to be tested in the liquid blood component, which includes:
    (a) a corpuscle/plasma separating part disposed at the lower end of the substrate, including a corpuscle fraction storing part to precipitate the blood corpuscle fraction upon exertion of centrifugal force and to store the corpuscle fraction, and a plasma fraction storing part located upper to the corpuscle fraction storing part to store the blood plasma;
    (b) a sensor part disposed at the upper end of the substrate, having sensor grooves housing sensors to analyze the components to be tested;
    (c) a plasma guiding flow channel to connect the corpuscle/plasma separating part;
    (d) an inlet for blood to introduce the whole blood sample to the corpuscle/plasma separating part;
    (e) a calibration solution reservoir to store a calibration solution for the calibration of sensors,
    (f) a calibration solution waste reservoir to store the calibration solution after the calibration of sensors,
    (g) a calibration solution introducing flow channel to connect the calibration solution reservoir and the sensor grooves, and
    (h) a calibration solution discharging flow channel to connect the sensor grooves and the calibration solution waste reservoir;
    wherein centrifugation can be carried out around a first centrifugal axis which is located upper to the corpuscle fraction storing part and lower to the upper end of plasma fraction storing part;
    while centrifugation can be carried out around a second centrifugal axis, which is located within or closer to the sensor part than corpuscle/plasma separating part; and
    wherein the calibration solution reservoir is located on the lower side of the sensor part and on the upper side of the first centrifugal axis, and the calibration solution waste reservoir is located on the upper side of the sensor part.

2. The blood analysis apparatus according to claim 1, wherein the corpuscle/plasma separating part is formed into a U-shaped flow channel, while the corpuscle fraction storing part is formed at the bend of the lower end of the U-shaped flow channel, and the plasma fraction storing part is formed on the upper side thereof.

3. The blood analysis apparatus according to claim 2, wherein the corpuscle/plasma separating part is formed to protrude downward from the lowermost part of the U-shaped flow channel, and the capacity of the corpuscle/plasma separating part is larger than the amount of the corpuscle fraction of the whole blood sample introduced into the U-shaped flow channel.

4. The blood analysis apparatus according to claim 2, wherein the inlet for blood is formed on a side wall of the U-shaped flow channel, upper to the plasma fraction storing part.

5. The blood analysis apparatus according to claim 2, wherein an air venting flow channel is formed to be connected to the U-shaped flow channel.

6. The blood analysis apparatus according to claim 1, wherein the sensor part has a plurality of sensor grooves housing sensors which respectively analyze various components to be tested.

7. The blood analysis apparatus according to claim 6, wherein the plurality of sensor grooves are arranged in a circumferential shape around the second centrifugal axis.

8. The blood analysis apparatus according to claim 1, wherein the inlet for plasma, the corpuscle/plasma separating part, the plasma guiding flow channel and the sensor grooves have been respectively subjected to hydrophilization.

9. The blood analysis apparatus according to claim 8, wherein the calibration solution reservoir, the calibration solution waste reservoir, the calibration solution introducing flow channel and the calibration solution discharging flow channel have been respectively subjected to hydrophilization.

10. The blood analysis apparatus according to claim 1, wherein the calibration solution discharging flow channel is a capillary valve.

11. The blood analysis apparatus according to claim 1, wherein the sensors are electrochemical sensors.

12. The blood analysis apparatus according to claim 1, wherein the inlet for blood is capable of mounting thereon a blood collecting instrument which stores collected blood.

13. A blood analysis method comprising the following steps:

(1) providing a blood analysis apparatus, which includes a corpuscle/plasma separating part disposed at the lower end of the substrate, including a corpuscle fraction storing part to precipitate the blood corpuscle fraction under the action of centrifugal force and to store the corpuscle fraction, and a plasma fraction storing part located on the upper side of the corpuscle fraction storing part to store the blood plasma; a sensor part disposed at the upper end of the substrate, having sensor grooves housing the sensors to analyze the components to be tested; a plasma guiding flow channel connecting the corpuscle/plasma separating part and the sensor part; an inlet for blood to introduce a whole blood sample to the corpuscle/plasma separating part; a calibration solution reservoir to store a calibration solution for calibration of the sensors; a calibration solution waste reservoir to store the calibration solution after the calibration of sensors; a calibration solution introducing flow channel to connect the calibration solution reservoir and the sensor grooves; and a calibration solution discharging flow channel to connect the sensor grooves and the calibration solution waste reservoir;

(2) introducing the calibration solution in the calibration solution reservoir into the sensor grooves by centrifuging the blood analysis apparatus around a first centrifugal axis which is located upper to the corpuscle fraction storing part and lower to the upper end of the plasma fraction storing part;

(3) performing calibration of the sensors;

(4) discharging the calibration solution in the sensor grooves to the calibration solution reservoir by centrifuging the blood analysis apparatus around the first centrifugal axis;

(5) performing separation of the blood corpuscles and blood plasma in the corpuscle/plasma separating part, and precipitating the blood corpuscle fraction in the corpuscle fraction storing part, by introducing a whole blood sample into the corpuscle/plasma separating part and centrifuging the blood analysis apparatus around a second centrifugal axis, which is located closer to the sensor part than the corpuscle/plasma separating part;

(6) conveying the blood plasma fractionated in the plasma fraction storing part to the sensor grooves by centrifuging the blood analysis apparatus around the first centrifugal axis; and (7) performing analysis of the liquid component of the blood plasma in the sensor grooves by means of the sensors.

14. The blood analysis method according to claim 13, wherein the gravitational acceleration exerted on the sensors is 500 G or less during the centrifugation performed at steps (2), (4) and (6).

15. The blood analysis method according to claim 13, wherein during the centrifugation performed at step (5), the gravitational acceleration exerted on the corpuscle/plasma separating part is 1000 G or greater, while the gravitational acceleration exerted on the sensors is 500 G or less.

16. A blood analysis method comprising the following steps:

(1) providing a blood analysis apparatus, which includes a corpuscle/plasma separating part disposed at the lower end of the substrate, including a corpuscle fraction storing part to precipitate the blood corpuscle fraction under the action of centrifugal force and to store the corpuscle fraction, and a plasma fraction storing part located on the upper side of the corpuscle fraction storing part to store the blood plasma; a sensor part disposed at the upper end of the substrate, having sensor grooves housing the sensors to analyze the components to be tested; a plasma guiding flow channel connecting the corpuscle/plasma separating part and the sensor part; an inlet for blood to introduce a whole blood sample to the corpuscle/plasma separating part; a calibration solution reservoir to store a calibration solution for calibration of the sensors; a calibration solution waste reservoir to store the calibration solution after the calibration of sensors; a calibration solution introducing flow channel to connect the calibration solution reservoir and the sensor grooves; and a calibration solution discharging flow channel to connect the sensor grooves and the calibration solution waste reservoir;

(2) introducing the calibration solution in the calibration solution reservoir into the sensor grooves by centrifuging the blood analysis apparatus around a first centrifugal axis which is located upper to the corpuscle fraction storing part and lower to the upper end of the plasma fraction storing part;

(3) performing calibration of the sensors;

(4) discharging the calibration solution in the sensor grooves to the calibration solution reservoir by centrifuging the blood analysis apparatus around the first centrifugal axis;

(5) performing separation of the blood corpuscles and blood plasma in the corpuscle/plasma separating part, and precipitating the blood corpuscle fraction in the corpuscle fraction storing part, by introducing a whole blood sample into the corpuscle/plasma separating part and centrifuging the blood analysis apparatus around a second centrifugal axis, which is located closer to the sensor part than the corpuscle/plasma separating part;

(6) conveying the blood plasma fractionated in the plasma fraction storing part to the sensor grooves by introducing an external gas under pressure through the air venting flow channel; and (7) performing analysis of the liquid component of the blood plasma in the sensor grooves by means of the sensors.

17. The blood analysis method according to claim 16, the gravitational acceleration exerted on the sensors during the centrifugation performed at steps (2) and (4) is 500 G or less.

18. The blood analysis apparatus according to claim 2, wherein the sensor part has a plurality of sensor grooves housing sensors which respectively analyze various components to be tested.

19. The blood analysis apparatus according to claim 3, wherein the sensor part has a plurality of sensor grooves housing sensors which respectively analyze various components to be tested.

20. The blood analysis apparatus according to claim 4, wherein the sensor part has a plurality of sensor grooves housing sensors which respectively analyze various components to be tested.

21. The blood analysis apparatus according to claim 5, wherein the sensor part has a plurality of sensor grooves housing sensors which respectively analyze various components to be tested.

* * * * *